United States Patent [19]
Cusak et al.

[11] Patent Number: 5,372,946
[45] Date of Patent: Dec. 13, 1994

[54] BLOOD COAGULATION TIME TEST APPARATUS AND METHOD

[75] Inventors: Robert Cusak, Edison; Frank M. Laduca, East Brunswick; Robert J. Samo, Lakewood, all of N.J.

[73] Assignee: International Technidyne Corporation, Edison, N.J.

[21] Appl. No.: 178,060

[22] Filed: Jan. 6, 1994

Related U.S. Application Data

[62] Division of Ser. No. 988,672, Dec. 10, 1992, Pat. No. 5,302,348.

[51] Int. Cl.$^5$ .............. G01N 21/03; G01N 33/86
[52] U.S. Cl. ......................... 436/69; 436/149; 436/165; 436/807; 435/13; 435/291; 422/102; 73/54.02; 356/246
[58] Field of Search ............ 436/46, 63, 69, 807, 436/80.8, 149, 165; 435/13, 287, 810, 970, 291; 422/99, 102; 73/54.02, 54.26, 54.27, 54.31, 54.35; 356/246

[56] References Cited

U.S. PATENT DOCUMENTS

| | | | |
|---|---|---|---|
| 3,486,859 | 12/1969 | Greiner et al. | 422/73 |
| 5,039,617 | 8/1991 | McDonald et al. | 436/69 |
| 5,147,606 | 9/1992 | Charlton et al. | 422/56 |
| 5,223,219 | 6/1993 | Subramanian et al. | 422/55 |
| 5,225,163 | 7/1993 | Andrews | 422/61 |

*Primary Examiner*—David A. Redding
*Attorney, Agent, or Firm*—Arthur L. Plevy

[57] ABSTRACT

The present invention is an apparatus and method for performing a coagulation time test on a sample of blood wherein the blood is deposited in a fluid reservoir and disposable cuvette. Within the cuvette is formed a capillary conduit have at least one restricted region. The cuvette is inserted into a testing machine which engages the cuvette and draws blood from the fluid reservoir into the capillary conduit. The blood is then caused to reciprocally move within the capillary conduit whereby the blood is forced to traverse the restricted region. The testing machine measures the time required each time the blood is caused to traverse the restrict region. When a measured time is a predetermined percentage longer than an immediately preceding time, coagulation is considered to have occured and the overall coagulation time is displayed to the operator.

17 Claims, 9 Drawing Sheets

BLOOD COAGULATION TIME TEST APPARATUS AND METHOD

This is a division of application Ser. No. 07/988,672, filed Dec. 10, 1992, now U.S. Pat. No. 5,302,348.

FIELD OF THE INVENTION

The present invention relates to a disposable cuvette for retaining a sample of blood and an automated test apparatus and method for analyzing the sample of blood within the cuvette to determine a coagulation time for the sample of blood.

BACKGROUND OF THE INVENTION

The coagulation of blood is necessary to in order to stop both internal and external bleeding. However, it is often desirable to alter the natural coagulation characteristics of blood while performing certain medical procedures. For example, during such surgical procedures the uninhibited coagulation of the blood can cause blood clots which may result in severe medical complications to the patient. Thus, it is desirable to suppress the natural coagulation process during the surgical procedure. However, upon the completion of the surgical procedure, it is desirable for the patient's blood to regain its natural coagulation characteristics. As such, the blood will again be able to clot and heal incisions and stop any internal or external bleeding.

In an attempt to scientifically control the coagulation characteristics of a persons blood, pharmacological agents have been developed that modify the inherent ability for a patient's blood to clot. A common substance usd to prolong the clotting time of a patient's blood is heparin. Heparin is a naturally occurring polysaccharide sulfuric acid ester found especially in lung, liver and intestinal tissue and has the ability in certain circumstances to prolong the clotting time of blood. Commercially available heparin is derived from animal tissues principally porcine intestine or bovine lung. As presently understood, commercially processed heparin is complex substance and its pharmacological activity per unit weight may vary depending on the characteristics of a specific batch of material. Due to the inconsisting of commercially produced heparin, heparin is sold with its biological potency expressed in U.S.P. units, where U.S.P. units are related to the clot formation inhibition of heparin mixed with sheep plasma.

When the effects of heparin on a patient's blood is no longer desired, it is commonplace to administer a substance known as protamine to the heparinized patient. Protamines are simple strongly basic proteins of relatively low molecular weight. These proteins are water soluble, not coagulated by heat and yield only amino acids, chiefly arginine when hydrolyzed.

Protamine is a naturally occurring material and is commercially available to the medical profession as an extract from certain fish (salmon) tissue. The purity and therefore the physiological potency of commercial protamine preparations, for reasons not well understood, have been shown to vary from batch to batch. Protamine is dispersed on a weight basis. Protamine, while of different chemistry than heparin, also has the property of prolonging the blood clotting time in humans.

Heparin and protamine are reactive with each other on a stoichiometric basis. Heparin is an anionic substance and protamine is a cationic substance. When the two substance are mixed in blood (either in vivo or a test tube) they react quantitatively to form a neutral (and physiologically inactive) entity. Medical personnel therefore infuse protamine at the conclusion of a surgical procedure, to neutralize heparin in patient's blood and restore normal, baseline blood clotting ability.

Protamine, however, as previously discussed, is itself an anticoagulant and if excess protamine is infused, hemostasis will not be achieved. Further complications can result from the fact that protamine may be toxic to some individuals. Protamine is also reportedly capable of including an allergic response in certain patients.

Since the amount of heparin in a patient's blood is critical, and since heparin varies in potency from batch to batch and patient to patient, measuring an administered dosage is insufficient in predicting the clotability characteristics of a patient's blood caused by the heparin. Similarly, since the potency of protamine also varies from batch to batch and patient to patient, merely measuring the administered dosage does not predict the effectiveness of the protamine on a given patient. Consequently, since dosage measuring is inconclusive, the blood of a patient must be constantly monitored and tested in order to accurately determine the effects of administered heparin, protamine or like compounds on the coagulation characteristics of a patient's blood.

The prior art is replete with various apparatus and methods for measuring the coagulation time of blood samples. For example, a method and apparatus for detecting blood coagulation is shown in U.S. Pat. No. 4,797,369 which issued on Jan. 10, 1989, entitled METHOD AND APPARATUS FOR DETECTING A BLOOD CLOT to Michael Mintz, and assigned to the assignee herein. In that particular patent, there is disclosed the technique for measuring clot time whereby a sample of whole blood or blood plasma is dispersed into two or more zones. The zones are separated and brought together repeatedly, such that the blood sample is divided into multiple parts each associated with a zone. The parts are then rejoined into a single part and the process of separation and joining continues. During the process, a liquid bridge between the separated parties is initially supported by surface tension, but initially collapses at the point of maximum zonal separation. When a fibrin clot is entrained within the rejoined parts, it will align in a direction parallel to the direction of the relative motion between the zones. In this manner, a thread appears between the parts as they are being separated. This thread is indicative of a clot, which clot is capable of being detected by visual or electrical means.

U.S. Pat. No. 3,486,859 entitled BLOOD ANALYZING METHOD AND APPARATUS issued on Dec. 30, 1969 to R. Greiner et al. This patent depicts a blood analyzing method and apparatus including a double arm holder having blood liquid reactant chambers which communicate with each other via a small capillary conduit. An air pump is provided for applying pressure changes to one of the chambers to effect periodic mixing of the liquids via the capillary conduit. An indicator means are included to detect the progressive restriction of the capillary conduit upon coagulation of the blood.

U.S. Pat. No. 3,695,842 entitled METHOD AND SYSTEM FOR ANALYZING A LIQUID issued on Oct. 30,1972 to M. D. Mintz, and assigned to the assignee herein. The patent describes in detail a magnetically coupled mechanical blood clot detection system wherein a variable conductance device is disposed adjacent to a zone containing a liquid and member of ferromagnetic flux lines is formed between the zone and the member. A predetermined variation in the conductance of the device is detected upon change in the magnetic flux lines when the liquid transforms itself and the member is displaced. The signal is produced at the time the predetermined variation in conductance has been detected.

An improved system means for measuring clotting time is disclosed in U.S. Pat. No. 3,836,333 entitled "SYSTEM FOR TIMING THE COAGULATION OF BLOOD" issued to Michael D. Mintz, on Oct. 30, 1972 and assigned to International Technidyne Corporation, the assignee herein. An electromagnetic bias coil, which is wound around the reed switch, provides stead-state magnetic flux lines that supplement the flux lines provided by the permanent magnet. When the density of the flux lines passing through the reed switch decreases, as a result of the magnet being displaced, the reed switch opens. The bias coil also provides a magnetic pulse, which forces the reed switch to a closed state. This system is manufactured under the trademark HEMOCHRON by International Technidyne Corporation at Edison, N.J.

U.S. Pat. No. 3,890,098 entitle MACHINE FOR THE DETERMINATION OF PROTHROMBIN TIME AND P.T.T. issued on Jun. 17, 1975 to E. Moreno. This patent describes a reactive material which is placed in a cup which communicates with a second cup via a restricted orifice. Plasma is placed in the second cup and the reactive material and plasma are moved from cup to cup by a pump until coagulation of the plasma takes place. Means are then provided for stopping the motion of the mixture of reactive material and plasma. Other means are provided for measuring the time required for coagulation.

U.S. Pat. No. 3,951,606 entitled APPARATUS FOR PROTHROMBIN TESTING issued on Apr. 20, 1976 to R. Moyer et al. This patient shows manually operable, disposable device which can measure coagulation rates. The device is a tube of a uniform bore which can accommodate a sample and contains appropriate amounts of lyophilized reagents required to conduct individual tests such as that for prothrombin time. Calibration marks on the tube are correlated in terms of these times and the position in which a liquid sample becomes immobilized as it descends down the tube corresponds to the test time. The rate of descent of the liquid is controlled by a limiting orifice or constriction or by inclining the tube to the vertical axis.

U.S. Pat. No. 4,197,734 entitled APPARATUS FOR DETERMINING BLOOD CLOTTING TIME issued on Apr. 15, 1980 to A. Rosenberg. This patent describes an apparatus which is capable of determining the clotting time of blood. The apparatus includes a support frame which supports a syringe containing a blood sample and a turntable adapted to rotate at a normal rate of speed. Blood from the syringe drops onto the turntable where the clotting time is automatically and graphically depicted by a chart rotatively carried upon the turntable. The apparatus can also be employed to determine variations in the viscosity of blood plasma and other fluids.

U.S. Pat. No. 4,725,554 entitled METHOD FOR MEASURING BLOOD COAGULATION TIME issued on Feb. 16, 1988 to K. Schildkenecht. This patent shows a method for measuring the coagulation time of a blood sample, in which a sample reagent mixture is formed by introducing the sample and at least one reagent into a cuvette. The sample reagent mixture is moved in a stationary cuvette so that the mixture flows back and forth around an edge projecting in to the cuvette whereby a clot forms and is detected on this edge.

U.S. Pat. No. 4,659,550 entitled METHOD AND APPARATUS FOR MEASURING BLOOD COAGULATION TIME is the parent of U.S. Pat. No. 4,725,554 and essentially describes the same system further utilizing photocell detectors to determine a clot formation.

As one can see from the above, there are may different types of systems all of which are operative to detect the formation of a clot and to provide an indication of coagulation time. However, many of the prior art devices are complicated and difficult to manufacture. As such, it is a primary objective of the present invention to provide a blood clot detection apparatus and method which is extremely simple to utilize and which is associated with a disposable covette to enable a plurality of such tests to be performed at low cost.

SUMMARY OF THE INVENTION

The present invention is an apparatus and method for performing a coagulation time test on a sample of blood. The apparatus includes a disposable cuvette that can be inserted into a test analysis machine whereby the blood being tested is isolated within the cuvette and never contaminates the test analysis machine. In a preferred embodiment, the cuvette includes a fluid reservoir for retaining a sample of blood. The blood within the fluid reservoir is accessed by two elongated conduits. The first conduit is the test conduit and is interconnected to the fluid reservoir in such a manner that only a predetermined volume of blood can be drawn into the test conduit regardless to whether the fluid reservoir had been properly filled or overfilled. Within the test conduit is formed at least one restricted region where the lumen of the test conduit narrows. The surface texture within the test conduit is essentially smooth except within the restricted regions where the surface texture of the test conduit is purposely roughened. The second conduit coupled to the fluid reservoir is the drain conduit. The drain conduit is coupled to the fluid reservoir in a manner that allows the drain conduit to draw the blood from the fluid reservoir that is not accessible by the test conduit.

The cuvette containing the test conduit and drain conduit is substantially transparent. As such, the presence of blood in either the test conduit or drain conduit can be readily optically detected. To test the blood sample in the fluid reservoir of the cuvette, the cuvette is inserted into a test analysis machine. Upon insertion, a pneumatic pump interconnects with test conduit and the drain conduit. Furthermore, the cuvette is positioned within the test analysis machine so that photoelectric sensors are positioned across the test conduit on either side of the restricted region.

Both the photoelectric sensors and the pneumatic pumps have a microprocessor control. To begin the coagulation time test on the blood sample, the pneumatic pump draws a predetermined volume of blood into the test conduit from the fluid reservoir. The pneumatic pump is then cycled causing the blood within the test conduit to reciprocally move from the a point on one side of the restricted region to a point on the opposite side of the restricted region and back again. As the blood sample is cycled back and forth, the photoelectric sensors are used to count the time it takes for the blood to traverse the narrowed region. As the blood passes the narrowed region, the blood begins to coagulate and clot along the roughened surface of the narrowed region, eventually occluding the normal of flow through the narrowed region. When the traversed time of one cycle of travel is a predetermined percentage longer than an immediately preceding cycle of travel, coagulation is considered to have occurred and the overall time for coagulation is displayed to the operator.

After the blood is drawn into the test conduit, residual blood from the fluid reservoir is drawn into the drain conduit. As such, when the cuvette is removed from the test analysis machine, no open reservoirs of blood remain which may spill during the manipulation of the cuvette.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Figure 1:
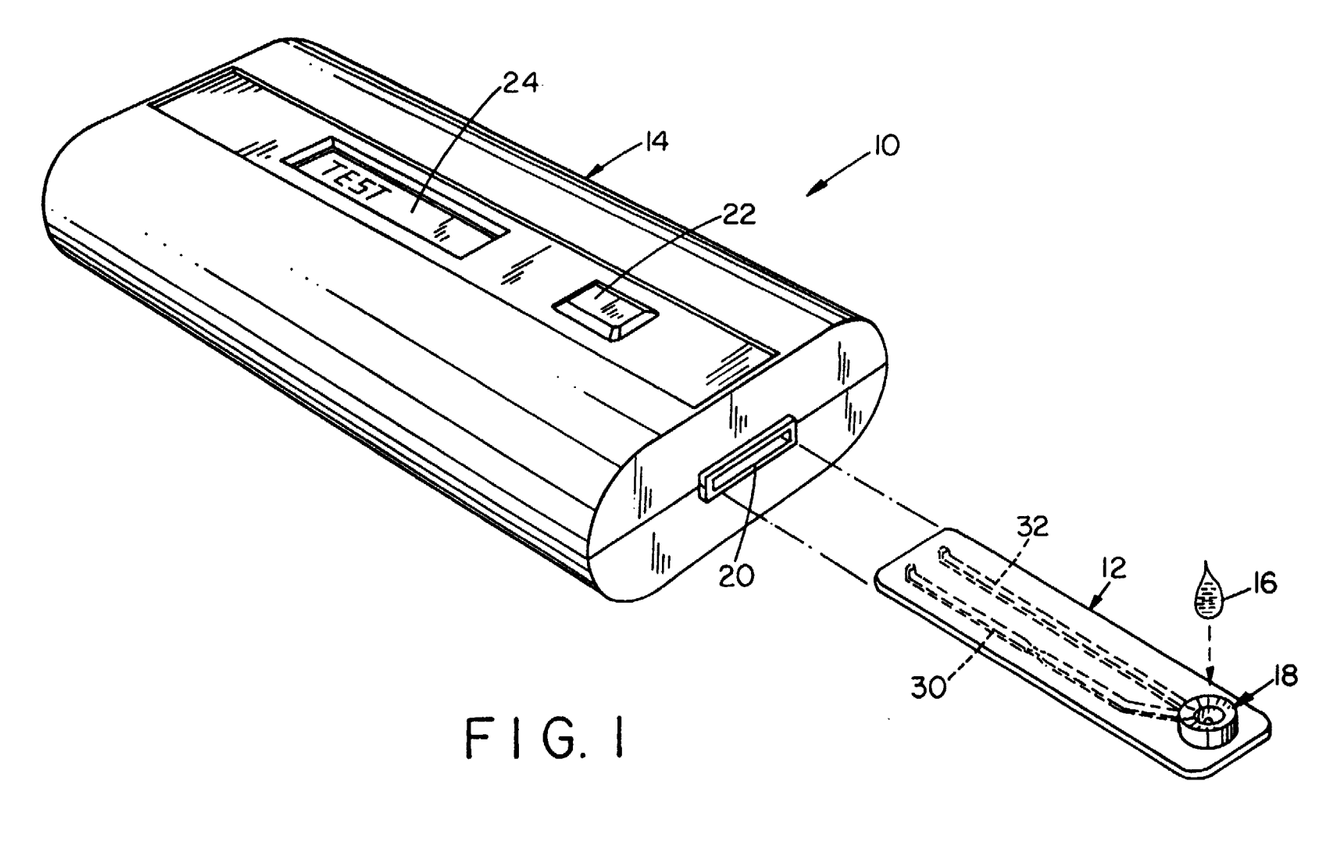
FIG. 1 is a perspective exploded view of one preferred embodiment of the present invention cuvette and blood coagulation time testing apparatus.

The present invention is an apparatus and method for determining the coagulation time for a given sample of whole blood. Referring to FIG. 1, there is shown one preferred embodiment of the present invention apparatus 10 consisting of a disposable cuvette 12 and a testing device 14. To utilize the present invention apparatus 10, a sample of blood 16 is placed within a fluid reservoir 18 on the disposable cuvette 12. The disposable cuvette 12 is then inserted into the testing device 14 through slot 20. Once the disposable cuvette 12 is within the testing device 14, the start button 22 is depressed by an operator. The testing device 14 tests the blood 16 within disposable cuvette 12 without contacting the blood 16. The time needed for the sample of blood 16 within the cuvette 12 to coagulate is then displayed on the display panel 24 atop the testing device 14. Once the coagulation test has been completed, the cuvette 12 can be removed from the testing device 14 and disposed of. Another cuvette with another sample of blood can then be immediately entered into the testing device 14 without the need to sterilize or otherwise clean the testing device 14.

Figure 2:
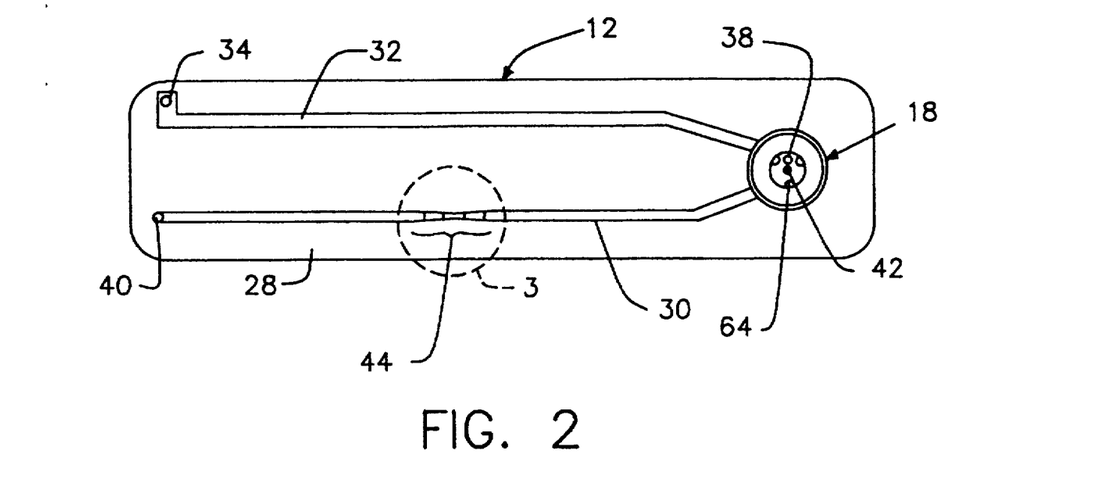
FIG. 2 is a top view of one preferred embodiment of the present invention cuvette.

The function of the individual components will now be described. Referring to FIG. 2 there is shown a top view of one preferred embodiment of a disposable cuvette 12. The cuvette 12 has a substantially planar base 28 formed from a transparent material. Within the planar base 28 are formed two channels or conduits a test capillary conduit 30 and a drain capillary conduit 32. The drain capillary conduit 32 terminates at one end with a drive aperture 34 which connects the lumen of the drain capillary conduit 32 to the ambient atmosphere. The opposite end of the drain capillary conduit 32 terminates at a fill aperture 38 within the fluid reservoir 18. The fill aperture 38 thereby permits fluid contained within the confines of the fluid reservoir 18 to flow into the drain capillary conduit 32.

Figure 3A:
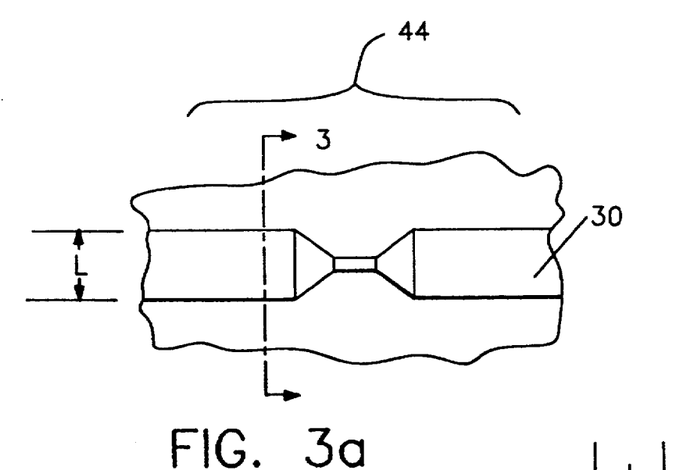
FIG. 3a is an enlarged view of the region of FIG. 2 contained within circle 3.
Figure 3B:
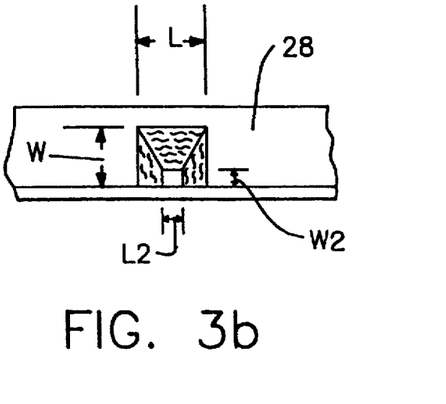
FIG. 3b is a cross-sectional view of FIG. 3a viewed along section line 3—3.

The test capillary conduit 30 also terminates at one end with a drive aperture 40 that interconnects the lumen of the test capillary conduit 30 to the ambient atmosphere. The opposite end of the test capillary conduit 30 terminates in the center of the fluid reservoir 18 at a standpipe 42. As such, fluid contained within the fluid reservoir 18 at a level above the height of the standpipe 42 flows through the standpipe and into the test capillary conduit 30. Proximate the center of the test capillary conduit 30 is formed a region 44 wherein the lumen of the test capillary conduit 30 narrows. Referring to FIGS. 3a and 3b it can be seen that within the narrow region 44 the length and width of the lumen of the test capillary conduit 30 is beveled, changing from a length L and a width W to a narrower length L2 and width W2 and then back again. Additionally, the surface texture of the test capillary conduit 30 within the narrowed region 44 is roughened. The narrower area within the conduit is a clot specific surface and may be plasma treated, chemically treated or otherwise treated or roughened to provide a more efficient clotting surface. The textured surface within the narrowed region 44 can be produced either by forming a texture on the surface of the mold used to form the cuvette 12 or texturing the narrowed region 44 after molding with any known etching technique.

Figure 4:
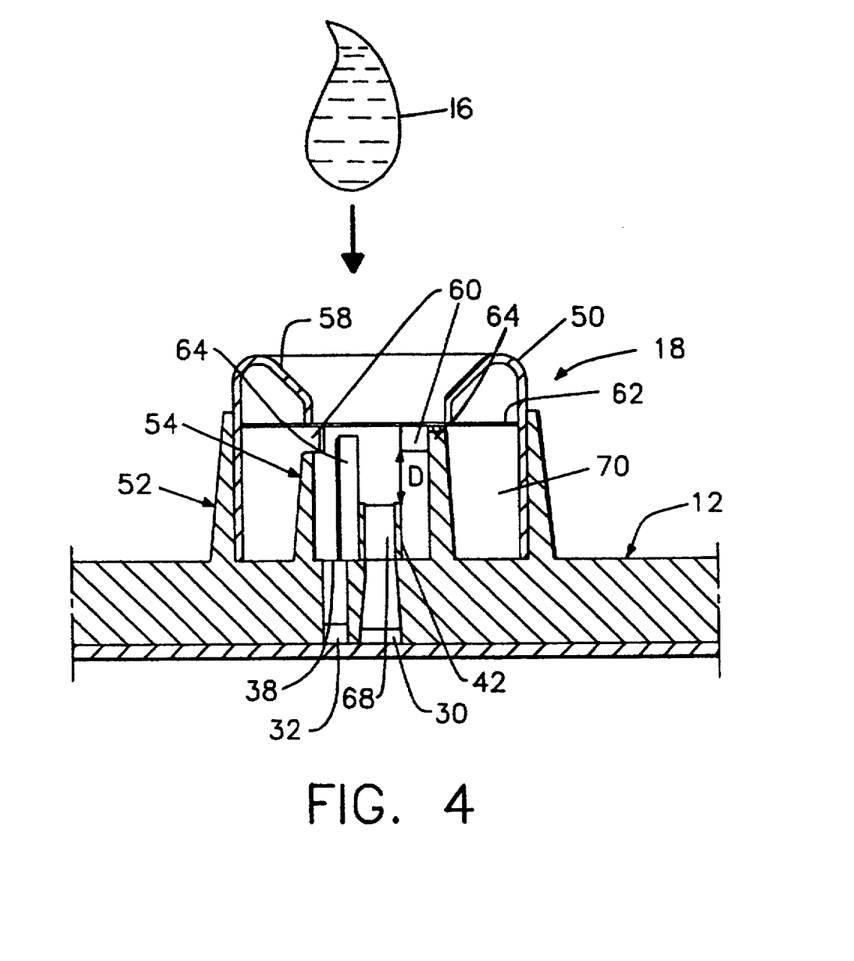
FIG. 4 is a cross-sectional view of the cuvette of FIG. 2 viewed along section line 4—4.

In FIG. 4 it can be seen that fluid reservoir 18 is not unistructural, but is rather formed by a cap member 50 being positioned between two concentric recepticles 52, 54 molded as part of the disposable cuvette 12. The outer recepticle 52 is annular in shape having a continuous peripheral wall. The cap member 50 is shaped to fit within the outer recepticle 52. The cap member 50 is annular in shape having a beveled surface 58 leading to a central aperture. The presence of the cap member 50 within the outer receptacle creates a beveled surface 58 at the top of the fluid reservoir 18 that leads into the center of the inner receptacle 54. The inner receptacle 54 is annular in shape but does not have a continuously formed peripheral wall. Rather, the height of the wall forming the inner receptacle 54 varies forming spaced overflow ports 60 between the inner receptacle 54 and the cap member 50. In a preferred embodiment, a gasket of absorbent material 62 may be placed between the cap member 50 and the top edge of the inner receptacle 54, the purpose of which will be later described.

Depending inwardly from the inner receptacle 54 are periodic filler stops 64. The filler stops 64 extend to a height within the inner receptacle 54 that is higher than the lower reaches of the overflow ports 60. In the center of the inner receptacle 54, is formed a standpipe 42. The standpipe 42 extends to a height that is a distance D below the height of the overflow ports 60. The lumen 68 of the standpipe 42 leads to the test capillary conduit 30. On the base of the inner receptacle 54, next to the standpipe 42, is formed a drain aperture 38. The drain aperture 38 leads to lumen of the drain capillary conduit 32.

To fill the fluid reservoir 18, blood 16 is directed into the inner receptacle 52 through the cap member 50. The blood 16 may be directed into the fluid reservoir 18 using a pipette, syringe or any other known method of application. However with some blood samples that contain infections decreases, it is desirable to minimize contact with the blood. Consequently, the filler stops 64 formed in the inner receptacle 52 are shaped to engage and stop the distal end of a syringe barrel at a predetermined height within the fluid reservoir 18. As such, a sample of blood within a syringe barrel can be directly administered to the cuvette 12 without having to transfer the blood sample to a pipette or other conventional sample administering device.

Once the sample of blood 16 has been adminsistered, the blood 16 fills the inner receptacle 52. Blood 16 at a level higher than the overflow ports 60, flows through the overflow ports 60 and into the interstice 70 between the inner receptacle member 54 and the outer receptacle member 52. The presence of the absorbent gasket 62 helps break the surface tension of the blood 16 by absorbing blood above the level of the overflow ports 60. As such, the blood 16 flows readily through the overflow ports 60. The blood 16 is prevented from flowing into the lumen of the standpipe 42 or the drain aperture 38 by the surface tension of the blood 16. Consequently, the blood 16 fills the inner receptacle 52 up to the level of the overflow ports 60 which is distance D above the aperture of the standpipe 44. As will later be explained, a pressure differential is applied to the test capillary conduit 30 and then to the drain capillary conduit 32. The pressure differential draws the blood 16 first into the test capillary conduit 30 and into the drain capillary conduit 32. The volume drawn into the test capillary conduit 30 is equal to the volume of blood 16 contained within the area specified by the distance D above the standpipe 42 and below the overflow ports 60. Consequently, despite the variations that occur in filling the fluid reservoir 18 with blood, as long as the fluid reservoir 18 is slightly overfilled an exactly measured sample of blood can be drawn into the test capillary conduit 30.

Figure 5:
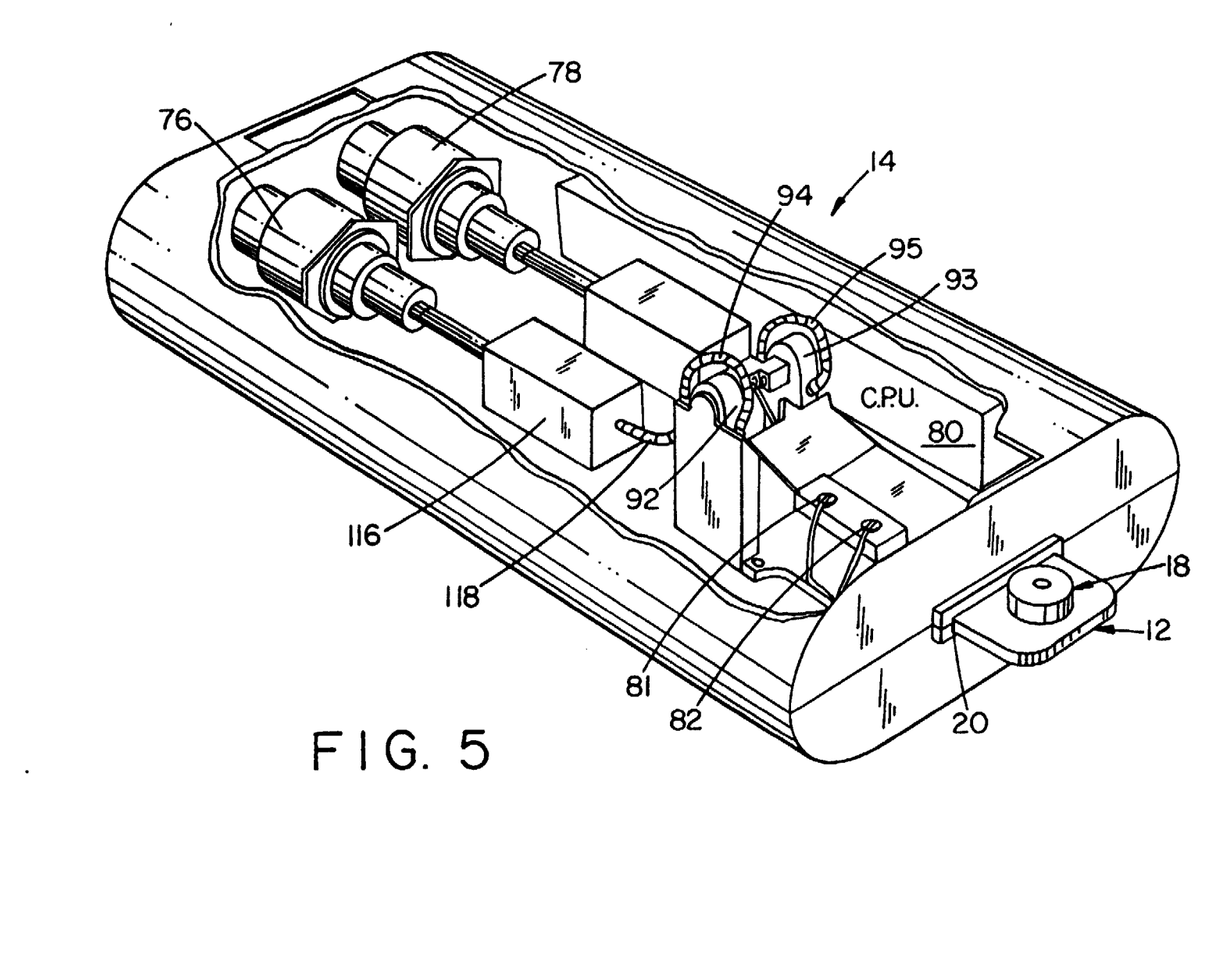
FIG. 5 is a selectively fragmented perspective view of the joined embodiment of FIG. 1 having selected internal components shown to facilitate consideration and discussion.
Figure 6A:
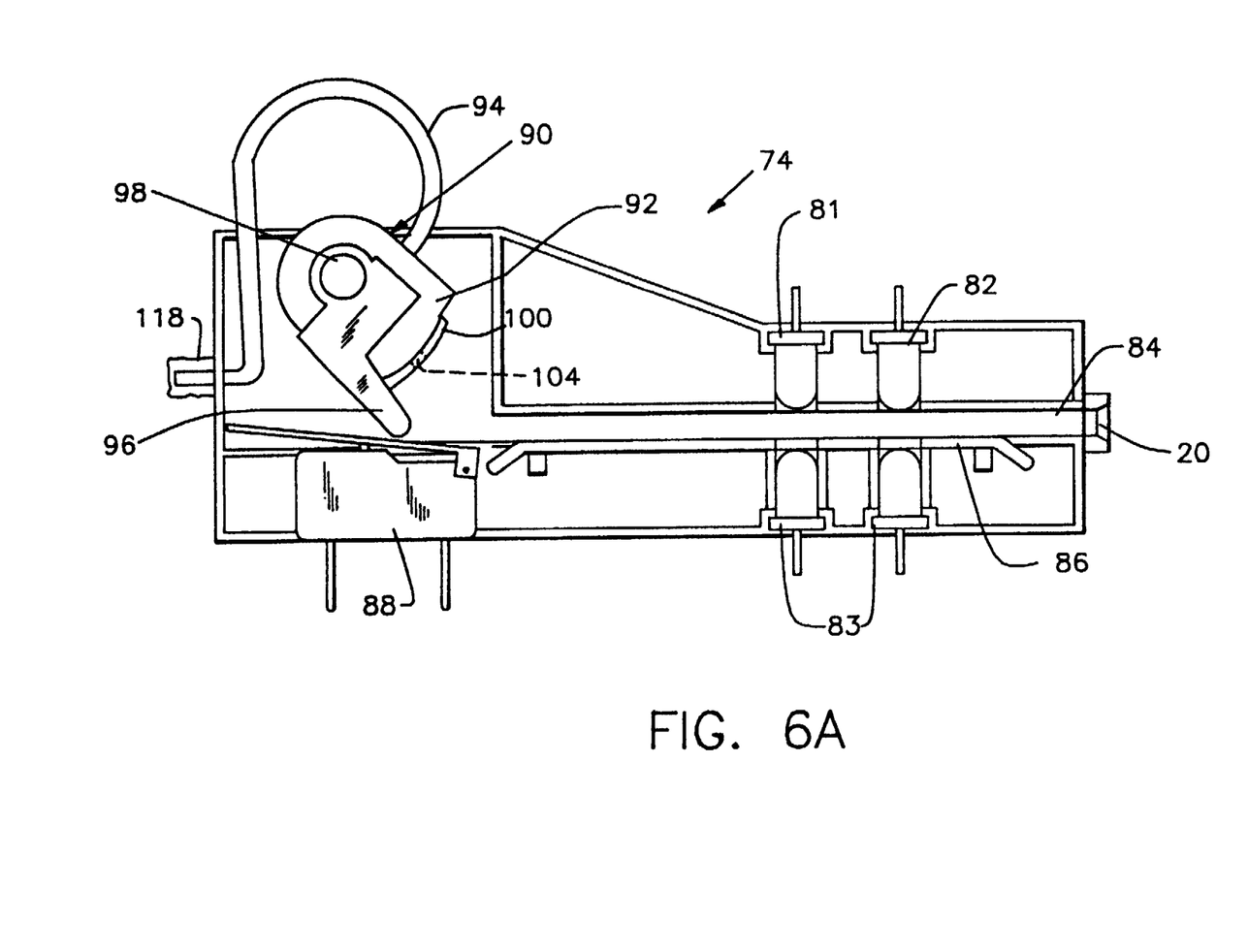
FIGS. 6a and 6b are cross-sections of one component of the present invention shown in FIG. 5 as viewed along section line 6—6.

In FIG. 5, the cuvette 12 is shown positioned within the test device 14. As can be seen from FIG. 5 the test device 14 is comprised of a testing interface 74 and two pneumatic pumps 76, 78, all of which are controlled by central logic designated as a central processing unit (CPU) 80. As will be later explained, the testing interface 74 pneumatically interconnects with the cuvette 12 and monitors a blood coagulation time test through the use of a plurality of photosensors 81, 82. The pneumatic pumps 76 and 78 provide periodically varying air pressure to the testing interface 74 in order to move the blood within the cuvette 12 for the purposes of the blood coagulation time test. Referring to FIG. 6a, it can be seen that the slot 20 through which the cuvette 12 enters the test device 14 leads into a channel 84 within the testing interface 74. Below the channel 84 is positioned a heating element 86 such as a foil heater or the like which is used to heat the cuvette 12 when it is within the channel 84. At the distal end of the channel 84, opposite the entrance slot 20, are positioned a proximity switch 88 and a pneumatic manifold assembly 90. The pneumatic manifold assembly 90 consists of two manifold members 92 and 95 of which only one is shown in FIG. 6 (both are shown in FIG. 5). The first manifold member 92 is pneumatically coupled to tube 94. Similarly the second manifold member 93 is pneumatically coupled to tube 95. Rocker arm members 96, extended downwardly from the manifold members 92, 93. The first manifold member 92 and the second manifold member 93 are joined and both the first and second manifold members 92, 93 have an orifice formed through their structures through which an axle rod 98 may pass. Consequently, the whole pneumatic manifold assembly 90 is pivotable rotatable around axle rod 98. At the base of each manifold member 92, 93 is positioned an elastomeric seal 100 having a central orifice 104. The central orifice 104 pneumatically communicates with the manifold member 92, 93 and the respective tubes 94, 95.

Proximate the center of the channel 84 are positioned a plurality of photoelectric sensors 81, 82 positioned on one side of the channel 84 directly across from light sources 83 which may be incandescent bulbs, light emitting diodes or the like. As will be later explained, the photoelectric sensors 81, 82 and light sources 83 are positioned within the testing interface 74 at positions that correspond to the test capillary conduit 30 in the cuvette 12. As such, light emissions from the light sources 83 to the photoelectric sensors 81, 82 must pass through to a material of the cuvette 12 and the test capillary conduct 30 within the cuvette 12.

Figure 6B:
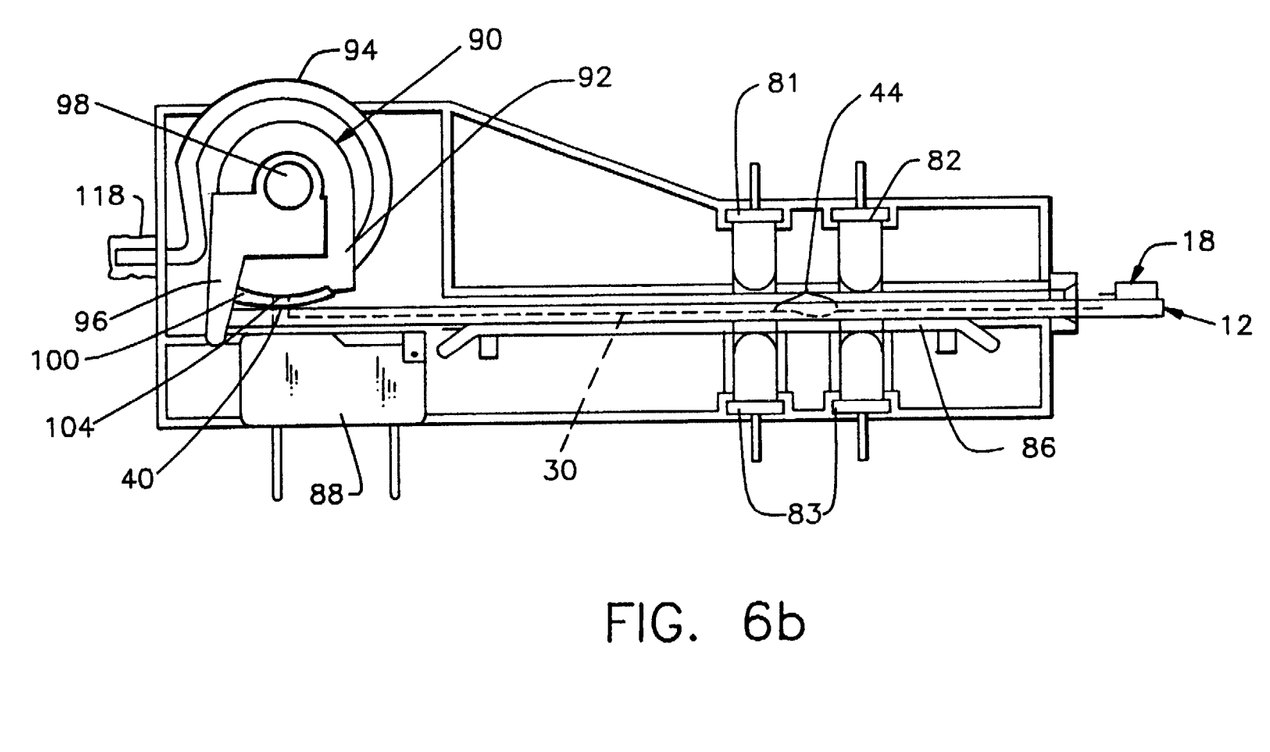

In FIG. 6b the testing interface 74 of FIG. 6a is depicted in combination with the cuvette 12. As can be seen, when the cuvette 12 is inserted into the channel 84, the cuvette 12 rotates the pneumatic manifold assembly 90 around the axil 98. Consequently, the elastomeric seals 100 on each of the two manifold members 92, 93 rotates against the material of the cuvette 12. As the elastomeric seals 100 rotate and contact the cuvette 12, the orifice on the elastomeric seal of the second manifold member 93 aligns with the drive aperture 34 of the drain capillary conduit 32. Similarly, the orifice 104 or the elastomeric seal 104 of the first manifold member 93 aligns with the drive aperture 40 of the test capillary conduit 30. The contact between the elastomeric seals and the cuvette 12 create an air tight seal, as such the first manifold member 92 becomes pneumatically coupled to the test capillary conduit 30 within the cuvette 12, and the second manifold member 93 becomes pneumatically coupled to the drain capillary conduit 32 within the cuvette 12.

The placement of the cuvette 12 fully within the testing interface 74 positions the narrowed region 44 and surrounding regions of the test capillary conduit 30 above the heating element 86. Consequently, blood contained within the cuvette 12 can be maintained at a constant temperature for testing, despite variations in the surrounding ambient temperature. The placement of the cuvette 12 within the testing interface 74 also positions the narrowed region 44 of the test capillary conduit 30 in between adjacent photoelectric sensors 81, 82. Consequently, the presence of blood in the test capillary conduit 30 on either side of the narrowed region 44 can be detected by the photoelectric sensors 81, 82. Furthermore, the placement of the cuvette 12 fully into the testing interface 74 engages the proximity switch 88, thereby notifying the CPU 80 that a cuvette 12 has been entered into the test device 14 for testing.

Figure 7:
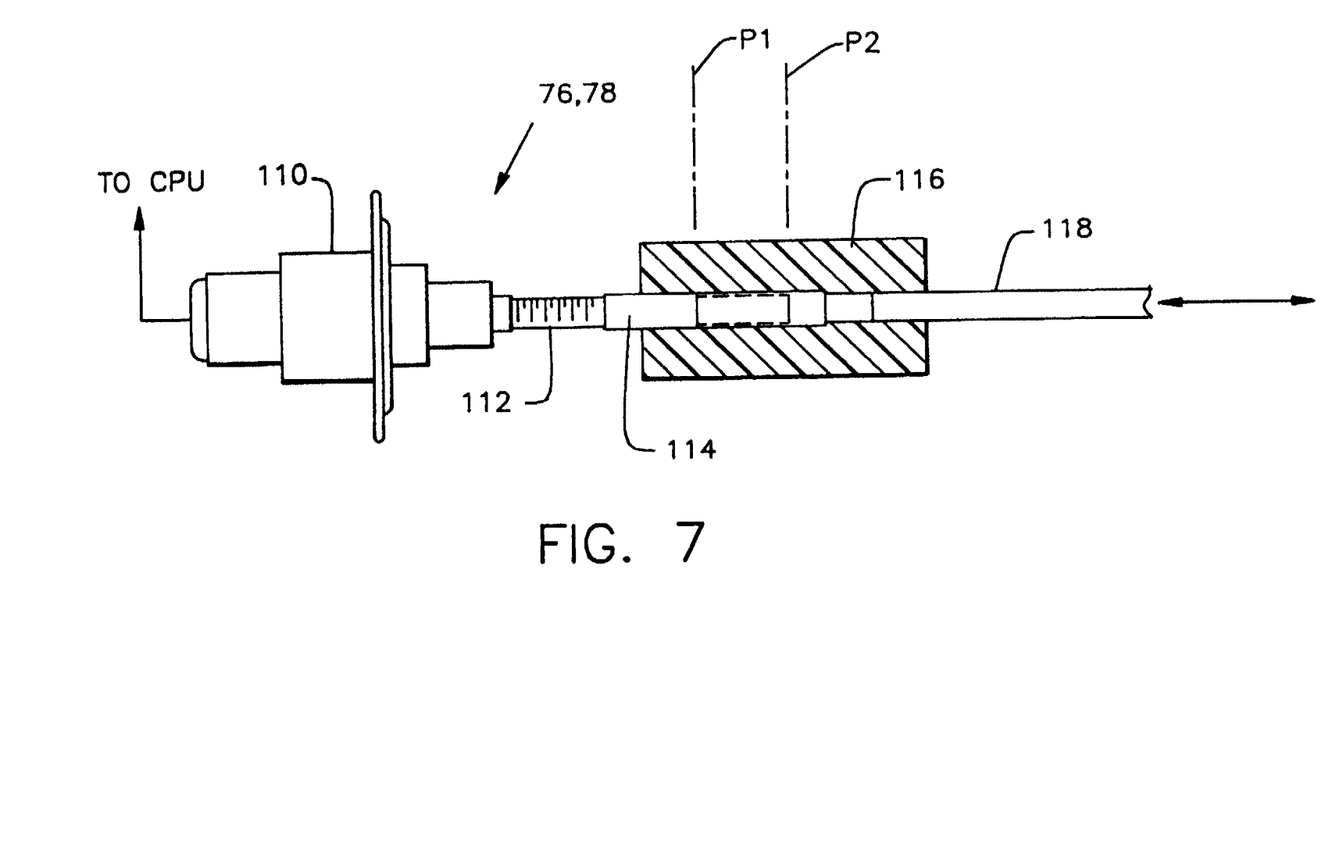
FIG. 7 is an insulated, selectively crossed sectional view of one preferred embodiment for the pneumatic pumps used in the present invention.

Referring to FIG. 7, there is shown one preferred embodiment for the pneumatic pumps 76, 78 used in the present invention. As can be seen from FIG. 7, each pneumatic pump 76, 78 consists of a bi-directional linear stepper motor 110, which can selectively drive a threaded shaft 112 back and forth along a linear axis. Such stepper motors are well known in the art and need not be described herein at length. The distal end of the threaded shaft 112 terminates in a plunger head 114. Consequently, the action of the stepper motor 110 on the threaded shaft 112 causes the plunger head 114 to reciprocate from a first position P1 to a second position P2. The plunger head 114 is positioned within a piston cylinder 116, whereby the plunger head 114 creates an air impervious seal with the piston cylinder 116. A tube 118 is coupled to the distal end of the piston cylinder opposite the stepper motor 110. The lumen of the tube 118 is coupled to the hollow of the piston cylinder 116. Consequently, as the plunger head 114 is reciprocally driven by the stepper motor 110, air is displayed through, or drawn from, the tube 118. Since the reciprocal movement of the stepper motor 110 can be exactly controlled, exacting volumes of air can be drawn or displaced by the pneumatic pumps 76, 78.

Returning to FIG. 6a, it can be seen that the tubes 118 leading from the pneumatic pumps 76, 78 interconnect with the first and second tubes 94, 95 on the pneumatic manifold assembly 90 respectively. As such, it should be understood that the action of first pneumatic pump 76 controls the air pressure in the first manifold member 92 and the action of the second pneumatic pump 78 controls the air pressure in the second manifold member 93.

Figure 8A:
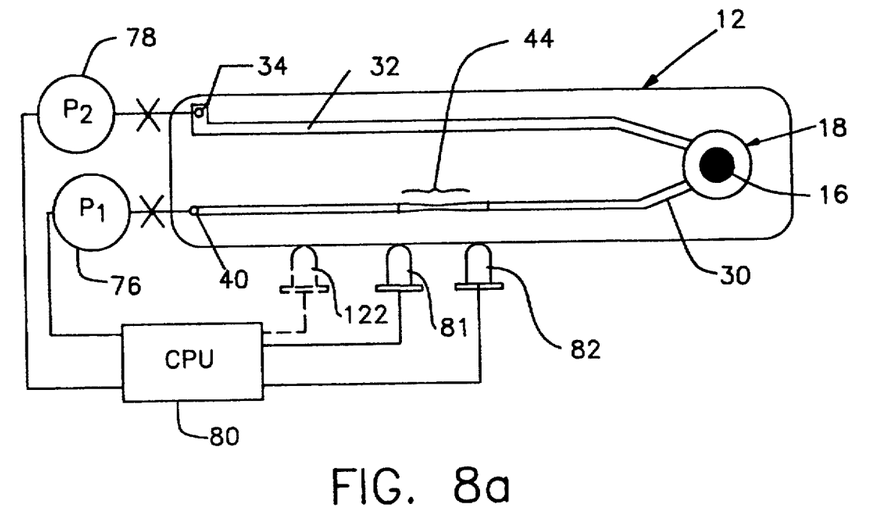
FIGS. 8a–8d are block diagrams showing the method of operation of the present invention.

Referring now to FIGS. 8a, 8b, 8c and 8d in conjunction with the previous illustrations, the operation of the present invention can be described. To begin a blood coagulation time test on a sample of blood, the cuvette 12 is inserted into the test device 14. Once in place, the fluid reservoir 19 is filled with a sample of blood 16. It should be understood that the fluid reservoir 18 can be filled prior to the insertion of the cuvette 12 into the test device 14 but this is less desirable due to the possibility of spillage as the filled cuvette 12 is moved to the test device 14. Once inserted in to the test device 14, the drain capillary conduit 32 and the test capillary conduit 30 become pneumatically coupled with the second and first pneumatic pumps 78, 76, respectively, in the manner previously described. In FIG. 8a, a newly inserted cuvette 12 is shown the sample of blood 16 being contained within the fluid reservoir 18. Neither pneumatic pump 78, 76 is operating. As such, the blood 16 remains in the fluid reservoir 18.

Figure 8B:
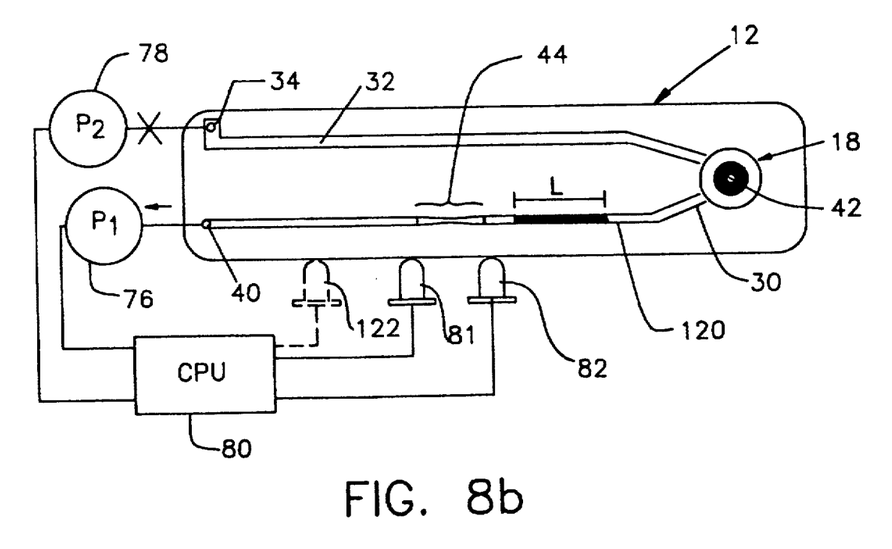

Once the cuvette 12 is in place and filled with blood 16, the start button 22 can be depressed. As such, the CPU 80 begins to control the first pneumatic pump 76 and begins monitoring the photoelectric sensor 82. Referring to FIG. 8b, it can be seen that the first pneumatic pump 76 draws air from the test capillary conduit 30. As such, the predetermined volume of blood available in the fluid reservoir 18 is drawn in to the test capillary conduit 30 through the standpipe 42. Consequently, a testing sample of blood 120 having a length L is formed in the test capillary conduit 30. As the blood testing sample 120 triggers the first photoelectric sensor 82, the CPU 80 begins a count on an internal clock.

Figure 8C:
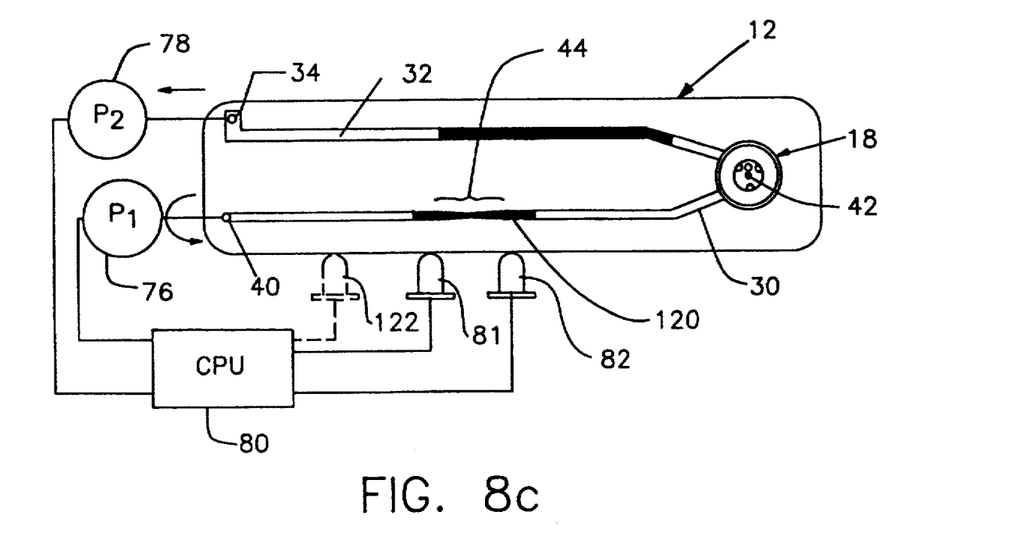

Referring to FIG. 8c, it can be seen that the first pneumatic pump 76 continues to draw the blood test sample 120 until the blood test sample 120 traverses the narrowed region 44 of the test capillary conduit 30 and triggers the second photoelectric sensor 81. When the second photoelectric sensor 81 is triggered, the CPU 80 stops its count and the value of the count is stored in memory. For example, if it takes five seconds for the blood test sample 120 to trigger the second photoelectric sensor 81 after the first photoelectric sensor 82, a count of five seconds is stored in the memory of the CPU 80. In addition to saving the time value in memory, when the blood test sample 120 triggers the second photoelectric sensor 81, the first pneumatic pump 76 reverses and displaces air into the test capillary conduit 30. At this point, the CPU 80 begins a second count on an internal timer.

The purpose of the third photoelectric sensor 122 is to sense any blood that has traveled too far into the test capillary conduit 30 toward the pneumatic pump 76. As such, the triggering of the third photoelectric sensor 122 may cause the CPU 80 to stop the first pneumatic pump 76 and prevent blood from being drawn out of the cuvette 12.

Additionally, at any time after the blood test sample 120 has been drawn into the test capillary conduit 30, the CPU 80 may activate the second pneumatic pump 78 and draw the remainder of the blood 16 within the fluid reservoir 18 into the drain capillary conduit 32. By removing the blood 16 entirely from the fluid reservoir 18, the cuvette 12 can now be handled without having to worry about blood spilling from the cuvette 112.

Figure 8D:
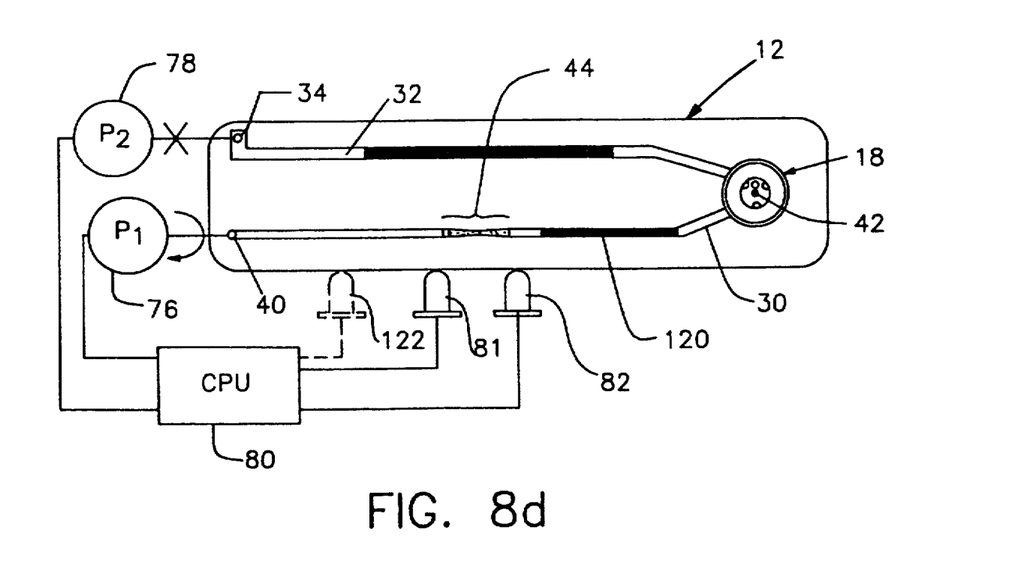

Referring to FIG. 8d, it can be seen that the first pneumatic pump 76 continues to displace air into the test capillary conduit 30 until the blood test sample 120 is again displaced beyond the first photoelectric sensor 82. Once the blood test sample 120 no longer obscures the first photoelectric sensor 82, the CPU 80 stops the second count saving the second count in its memory and comparing the second count to the previously saved first count as will be explained. The first pneumatic pump 76 is again reversed and the cycle is repeated thereby reciprocally moving the blood test sample back and forth past the narrowed region between the two photoelectric sensors 82, 81.

As the cycles of movement repeat, the blood test sample 120 begins to coagulate in the narrowed region 44 of the test capillary conduit 30. The coagulation is promoted by the roughened surfaces of the test capillary conduit 30 within the narrowed region 44. As such, with each cycle the occlusion presented by the narrowed region 44 increases. Consequently, once coagulation has begun, each cycle takes more time than the previous since the opening being traversed by the flowing blood test sample 120 becomes smaller. At the same time, the rate at which the column of blood is oscillated or driven back and fourth is decreased. The decrease is implemented on a time weighted basis such that the system resolution can be optimized to a percentage of total elapsed time. For example, continuously decreasing the rate of oscillation by 5% allows one to resolve fast forming clots within fractions of a second and slow forming clots (high heparin clots) within I 20 seconds of a 400 second test. This is important as one minimizes the defribrinization of the clot being found.

For each cycle the CPU 80 counts the time for the cycle and compares it to the previously cycle time. When any one cycle time is a predetermined amount of time longer than the previous cycle time, the CPU 80 considers coagulation to have occurred and the overall time for coagulation is displayed on the visual display means 24. For example, in one preferred embodiment of the present invention, it has been determined that a 125% change between subsequent cycle times indicates coagulation has occurred. As such, if one cycle took four seconds and the next cycle took five seconds, the CPU 80 would stop the test and display the elapsed time taken for coagulation to occur.

It should be understood that the embodiment described herein is merely exemplary and that a person skilled in the art may make many variations and modifications to the described embodiment utilizing functionally equivalent components to those described. More specifically, it should be understood that any shaped and constructed conduit path can be used in reciprocally cycling the blood test sample. As such, the placement of photoelectric sensors and the time differential between cycles need to determine coagulation may vary. One may utilize only one photosensor to detect the presence of clotted blood. As one can ascertain, upon the formation of a clot, blood would not move through the constricted area 44 and hence the sensor would not change state. All such equivalent components, variations and modifications are intended to be included within the scope of this invention as defined by the appended claims.

What is claimed is:

1. A cuvette for use with a drive means in determining a clotting time for a blood sample, comprising;
   a planar member having at least one enclosed conduit formed therein, said at least one conduit having an open distal end and proximal end and at least one restricted region positioned therebetween, wherein said at least one restricted region has a roughened surface texture that promotes the coagulation of blood flowing therepast, said distal end being selectively engagable with the drive means;
   a fluid reservoir for retaining said blood sample whereby a predetermined volume of blood is accessible by said proximal end of said at least one conduit, wherein said predetermined volume of blood is drawn into said at least one conduit and reciprocally moved back and forth across said at least one restricted region by the drive means, said clotting time being determined when said predetermined volume of blood clots and obstructs said at least one restricted region by a predetermined amount.

2. The cuvette according to claim 1, wherein at least one drain conduit is formed within said planar member, said drain conduit being interconnected to said fluid reservoir and engaged by the drive means whereby blood can be removed from said fluid reservoir into said at least one drain conduit after said predetermined volume of blood is drawn into said at least one conduit.

3. The cuvette according to claim 2, wherein said fluid reservoir includes a primary chamber and a secondary chamber, said blood sample being applied to said primary chamber wherein an excess of blood in said primary chamber overflows into said secondary chamber via overflow ports present between said primary chamber and said secondary chamber.

4. The cuvette according to claim 3, wherein said primary chamber has at least one standpipe positioned therein, said at least one standpipe interconnecting with said proximal end of said at least one conduit whereby said at least one standpipe extends upwardly within said primary chamber a predetermined distance below said overflow ports, said at least one drain conduit being interconnected to said primary chamber below said standpipe, whereby said at least one conduit means can draw blood from said primary chamber above said standpipe and below said overflow ports and said at least one drain conduit means can draw blood from said primary chamber below said standpipe.

5. The cuvette according to claim 1, wherein said cuvette is formed from a translucent material.

6. The cuvette according to claim 3, further including an annular cap member, said annular cap member fitting over said fluid reservoir covering said secondary chamber and having a sloped surface that directs said blood sample into said primary chamber, whereby the presence of said cap member over said secondary chamber prevents blood from spilling out of said second chamber as said cuvette is manipulated.

7. The cuvette according to claim 1, further including a stopping means within said fluid reservoir for stopping a discharging end of a syringe at a predetermined point within said fluid reservoir when said blood sample is applied to said fluid reservoir with said syringe.

8. A method of conducting a coagulation time test on a blood sample drawn from a patient, comprising the steps of:
   depositing said blood sample into a fluid reservoir;
   drawing a predetermined volume of blood from said blood sample into a capillary tube from said fluid reservoir wherein said capillary tube has at least one restricted region formed therein;
   reciprocating said predetermined volume of blood from a first position on one side of said restricted region to a second position on an opposite side of said restricted region and back again;
   counting the time elapsed each time said predetermined volume of blood reciprocates between said first position and said second position; and
   providing an indication to an operator when the time elapsed for one cycle of travel for the blood between said first position and said second position is a predetermined percentage longer then an immediately preceding cycle of travel.

9. The method according to claim 8, further including the step of draining blood from said fluid reservoir into a drain capillary tube after said step of drawing, thereby substantially emptying said fluid reservoir of said blood sample allowing said fluid reservoir to be manipulated without spillage of said blood sample.

10. The method according to claim 8, wherein said fluid reservoir and said capillary tube are contained within a disposable cuvette and further comprising the step of coupling said cuvette to a reciprocating drive means.

11. The method according to claim 8, wherein said restricted region has a roughened surface texture thereby promoting coagulation of said predetermined volume of blood in said roughened region as said predetermined volume of blood is reciprocated across said roughened region.

12. The method according to claim 9, wherein said fluid reservoir, said capillary tube and said drain capillary tube are contained within a disposable cuvette and further comprising the steps of coupling said capillary tube and said drain capillary tube to separate drive means.

13. The method of claim 8, wherein first photoelectric sensor is positioned at said first position and a second photoelectric sensor is positioned at said second position, wherein said first and second photoelectric sensors can detect the presence of said predetermined volume of blood in said capillary tube and wherein said step of counting is performed by a microprocessor coupled to said first and second photoelectric sensor that measures the time interval between the activation of said first and second photoelectric sensors by the reciprocating predetermined volume of blood.

14. The method according to claim 8, further including the step of heating said predetermined volume of blood in said capillary tube to a predetermined temperature.

15. The method according to claim 8, further including detecting if a portion of said predetermined volume of blood has been drawn beyond an acceptable point in said capillary tube and indicating to an operator the presence of said portion beyond said acceptable point.

16. The method according to claim 8, wherein said predetermined percentage is approximately 125 percent.

17. The method according to claim 8, wherein said step of reciprocating includes pneumatically reciprocating said predetermined volume of blood in said capillary tube.

* * * * *

UNITED STATES PATENT AND TRADEMARK OFFICE
CERTIFICATE OF CORRECTION

PATENT NO. : 5,372,946

DATED : December 13, 1994

INVENTOR(S) : Robert Cusack, Frank M. LaDuca and Robert J. Samo

It is certified that error appears in the above-identified patent and that said Letters Patent is hereby corrected as shown below:

On the title page, items

United States Patent [19] Cusak et al.

to —United States Patent [19] Cusack et al.—

[75] Inventors: Robert Cusak to —[75] Inventors: Robert Cusack—

Signed and Sealed this

Fourteenth Day of March, 1995

*Attest:*

BRUCE LEHMAN

*Attesting Officer*          *Commissioner of Patents and Trademarks*